United States Patent
Faehndrich et al.

(10) Patent No.: US 9,414,884 B2
(45) Date of Patent: Aug. 16, 2016

(54) INSTRUMENT SET FOR TREATING STENOSES OF THE SPINAL CANAL

(76) Inventors: Martin Faehndrich, Dusseldorf (DE); Florian Alfen, Wurzburg (DE)

(*) Notice: Subject to any disclaimer, the term of this patent is extended or adjusted under 35 U.S.C. 154(b) by 165 days.

(21) Appl. No.: 14/234,014

(22) PCT Filed: Jul. 23, 2012

(86) PCT No.: PCT/EP2012/064438
§ 371 (c)(1),
(2), (4) Date: Jan. 21, 2014

(87) PCT Pub. No.: WO2013/014131
PCT Pub. Date: Jan. 31, 2013

(65) Prior Publication Data
US 2014/0142379 A1 May 22, 2014

(30) Foreign Application Priority Data
Jul. 22, 2011 (DE) .................. 20 2011 103 583 U

(51) Int. Cl.
*A61B 18/14* (2006.01)
*A61B 1/06* (2006.01)
(Continued)

(52) U.S. Cl.
CPC .............. *A61B 18/148* (2013.01); *A61B 1/06* (2013.01); *A61B 17/0218* (2013.01); *A61B 17/1671* (2013.01); *A61B 17/32002* (2013.01); *A61B 17/1626* (2013.01); *A61B 17/1631* (2013.01); *A61B 17/1633* (2013.01);
(Continued)

(58) Field of Classification Search
CPC .......... A61B 18/14; A61B 1/06; A61B 17/16; A61B 18/148; A61B 17/1671

USPC .................. 600/104; 606/41, 47, 79–85, 170
See application file for complete search history.

(56) References Cited

U.S. PATENT DOCUMENTS

2005/0209622 A1  9/2005  Carrison
2005/0261692 A1  11/2005  Carrison et al.
(Continued)

FOREIGN PATENT DOCUMENTS

WO      00/76409 A1   12/2000
WO      2007/106740    9/2007
(Continued)

OTHER PUBLICATIONS

PCT Search Report, PCT/EP2012/064438, dated Nov. 2, 2012.
(Continued)

*Primary Examiner* — Christopher Beccia
(74) *Attorney, Agent, or Firm* — The Dobrusin Law Firm, PC

(57) ABSTRACT

An instrument set for the microinvasive treatment of stenoses of the spinal canal and/or other constrictions of the spinal canal, comprising
 a microinvasive access tube (1) having a distal end insertable into the body;
 an ablation device (2) having an ablation head (21) which can be accommodated in the access tube (1) and which can be directed out of the access tube (1) at the distal end and brought into at least one working position;
 a screening element (31) for screening the ablation head (21) in relation to the dura which can be accommodated in the access tube (1) and which can be directed out of the access tube (1) at the distal end and brought into at least one working position in which the screening element (31) laterally protrudes above the access tube (1).

20 Claims, 12 Drawing Sheets

(51) Int. Cl.
  *A61B 17/16* (2006.01)
  *A61B 17/02* (2006.01)
  *A61B 17/32* (2006.01)
  *A61B 17/00* (2006.01)
  *A61B 17/29* (2006.01)
  *A61B 17/34* (2006.01)

(52) U.S. Cl.
  CPC .......... *A61B 2017/00022* (2013.01); *A61B 2017/00221* (2013.01); *A61B 2017/00261* (2013.01); *A61B 2017/0256* (2013.01); *A61B 2017/0262* (2013.01); *A61B 2017/2927* (2013.01); *A61B 2017/3445* (2013.01)

(56) References Cited

U.S. PATENT DOCUMENTS

| | | |
|---|---|---|
| 2007/0027464 A1 | 2/2007 | Way et al. |
| 2010/0057087 A1 | 3/2010 | Cha |
| 2010/0286695 A1 | 11/2010 | Hannani et al. |

FOREIGN PATENT DOCUMENTS

| | | |
|---|---|---|
| WO | 2007/106740 A2 | 9/2007 |
| WO | 2008/027926 | 3/2008 |
| WO | 2008/027926 A2 | 3/2008 |
| WO | 2011/060077 | 5/2011 |
| WO | 2011/060077 A1 | 5/2011 |

OTHER PUBLICATIONS

Guigui, P.; Cardinne, L. Rillardon, L.; Morias, T.; Vuillemin, A.; Deburge, A.; Pre- and postoperative complications of surgical treatment of lumbar spinal stenosis: prospective analysis of 306 patients, Rev Chir Orthop Reparatrice Appar Mot., Jul. 29, 2002, 88, 669-677.
Hoogland, Thomas; van den Brekel-Dijkstra, Karolien; Schubert, Michael; Miklitz, Boris; Endoscopic Transforaminal Discectomy for Recurrent Lumbar Disc Herniation, Spine, Apr. 20, 2009, vol. 33, Issue 9, 973-978.
Telfeian, Albert E.; Veeravagu, Anand; Oyelese, Adetokunbo A.; Gokaslan, Ziya L.; A Brief History of Endoscopic Spine Surgery, Neurosurgical Focus, Feb. 2016, vol. 40, 1-5.
Chinese Office Action, Patent Application No. 201280046165,1, dated Sep. 24, 2015.
International Search Report and Written Opinion, Application No.: PCT/EP2012/064438 dated Nov. 2, 2012.

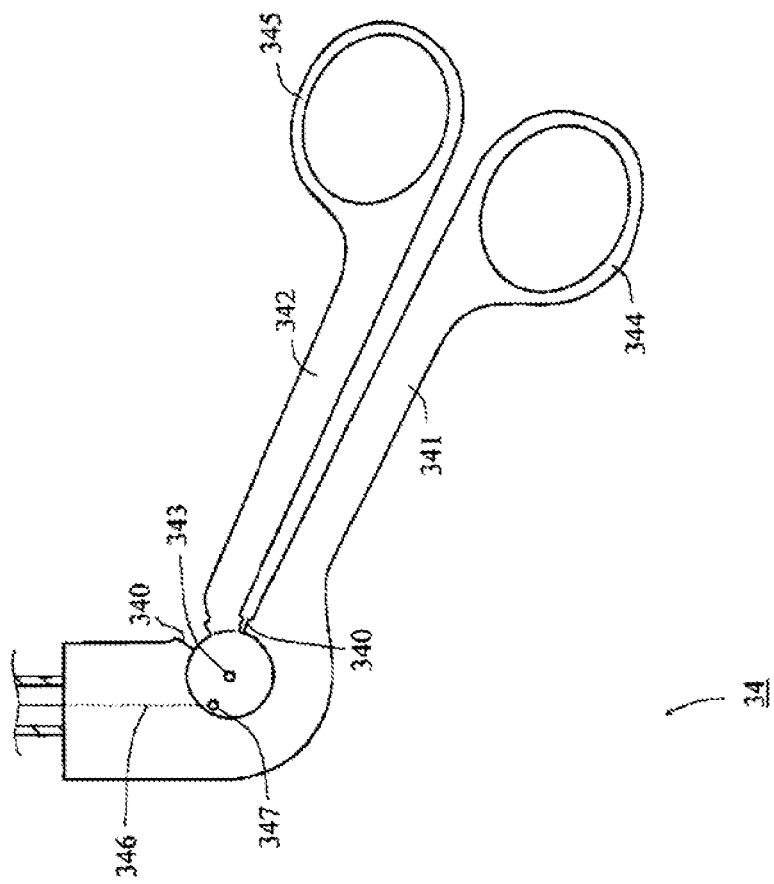
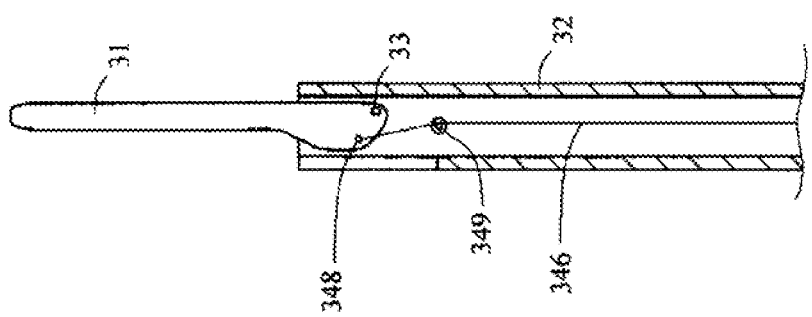
Fig. 9B
Fig. 9A

INSTRUMENT SET FOR TREATING STENOSES OF THE SPINAL CANAL

The invention relates to an instrument set for treating stenoses of the spinal canal.

Inside the spinal column composed of individual vertebrae the spinal cord extends. FIG. 1 shows a vertebra and the spinal cord in a cross sectional view. The individual vertebrae respectively comprise a massive ventral part (which is arranged so as to be directed towards the human abdomen), the vertebral body (WK), and a rear part, the vertebral arch (WB). Between the vertebral body and the vertebral arch, there is the vertebral foramen (WL). The vertebral foramens of the vertebrae form the spinal canal accommodating the spinal cord (R) which is i.e. referred to as the dura. To embed the spinal cord in the spinal canal tissue, ligaments are disposed between the vertebral body or the vertebral arch and the spinal cord. With increasing age, these tissue ligaments tend to harden and to, at the same time, gain volume, which is referred to as ossification. If such an ossification occurs on a larger scale a constriction of the spinal cord may occur which causes symptoms of paralysis and pain. Such constrictions caused by ossified tissue are referred to as stenoses of the spinal canal.

Particularly often, stenoses of the spinal canal develop at a tissue ligament disposed rearward between the vertebral arch and the spinal cord (directed towards the human back), the yellow ligament or ligamentum flavum (Lig). As can be seen in FIG. 1, the vertebral arch comprises two insertions connected to the vertebral body, the pedicels (P), in its vantral section, and the rear vertebral arch which is also referred to as the lamina (La) in the rearward section. Originating from the two transition points between the pedicels and the lamina, a transverse process (QF) protrudes in the lateral direction of the spinal column (laterally), respectively. Originating at the centre of the vertebral arch, the spinous process (DF) extends protruding in the rearward direction. Between the spinous process and each of the two transverse processes an articular process (GF) extends upwards in the longitudinal direction of the spinal column, and an articular process extends downwards. These articular processes, in cooperation with the articular processes of the adjacent vertebra, form the facet joints which are moved relative to each other via the vertebrae. The ligamentum flavum is located on the spinal canal side surface of the lamina including the articular processes.

To date, stenoses of the spinal canal are cured by surgical procedures in which the surgery starts at the centre of the back where the spinal column extends. In the process, first, the affected vertebral body is amply exposed by opening the skin and severing the muscle tissue surrounding the spinal column. Then that part of the lamina at which the stenoses of the spinal canal have developed is punched out of the vertebral body. This technique is referred to as microlaminectomy and is described, e.g., in "Pre- and postoperative complications of surgical treatment of lumbar spinal stenosis: prospective analysis of 306 patients" by Guigul, P. L. Cardinne, L. Rillardon, T Morais, A. Vuillemin, A, Deburge, Rev Chir Orthop Reparatrice Appar Mot. 88, 7: 669-677 (2002).

In the course of this surgery frequently one of the two halves of the lamina (hemilaminectomy) or even both halves of the lamina (laminectomy) have to be fully removed which leads to a substantial destabilisation of the vertebral body. Then, possibly, the spinal column has to be stabilised by connecting a plurality of vertebral bodies using sheet elements which are fixed by means of pedicel screws (osteosynthesis), particularly if a plurality of vertebral bodies are affected. This is disadvantageous in that the spinal column loses its mobility almost completely in the affected area. Since, to a substantial extent, muscle tissue has to be severed and punching out parts of the lamina leads to severe injuries of the surrounding tissue microlaminectomy is further associated with the usual disadvantages of severe surgical interventions. This includes dysfunctions in wound healing, risk of infection, prolonged convalescence, scar formation and the risks of anaesthesia. This means that elder people cannot undergo this surgery without thinking twice. Ultimately, it may result in dangerous, right up to fatal injuries if the screwed pedicel connection breaks owing to excessive stress, e.g. if the patient is an active athlete and unforeseeable movemeets of the vertebral body occur.

In connection with another medical condition of the spinal column, the herniated disc, socalled microinvasive surgical techniques are known. The problems encountered in case of a herniated disc are shown in FIG. 2. Between the individual vertebral bodies, the intervertebral discs (BS) serving as elastic buffers between the vertebral bodies are located. The intervertebral discs are composed of an outer ring consisting of connective tissue and cartilage, the annulus fibrosus (AF), and a gelatinous inner core, the nucleus (N). The nucleus may shift or leak as a result of ruptures of the annulus fibrosus (AF) which is referred to as a herniated disc (Vor). Above the transverse processes, lateral recesses are present in the vertebral bodies which are referred to as foramen intervertebrale (FI). Nerve fibres (NS) laterally branching off the spinal cord and lading to individual organs, parts of the muscle system, etc. extend through this recess. If a larger amount of the gelatinous substance of the nucleus leaks, this mass may exert pressure on the nerve cord laterally branching off the spinal cord in the area of the root and thus cause intense pain or symptoms of paralysis.

For treating these medical conditions, the endoscopic transforaminal nucleotomy was developed which is, for example, described in "Endoscopical foraminal removal of disc herniation" by T. Hoogland, J. Hallbauer, $4^{th}$ International Spine Symposium, Munich, September 1995. Starting from the side of the back, a microinvasive access path to the intervenebral disc is established through the foramen intervertebrale. An endoscope is inserted into this access path. Through the working passage of the endoscope, microtongs are introduced with the aid of which the leaked nucleus tissue constituting the herniated disc is removed to remedy the impairment of the nerve cord.

However, in spite of the most intense efforts of the professional circles, stenoses of the spinal canal could not be successfully remedied by means of microinvasive methods so far. The tongs developed for transforaminal nucleotomy are unfit for removing stenoses of the spinal canal. Furthermore, stenoses of the spinal canal are to be found in places which are presently not accessible without punching out parts of the vertebral body.

It is the object of the invention render the microinvasive treatment of stenoses of the spinal canal possible.

According to the invention this object is, on the one hand, solved by an instrument set for the microinvasive treatment of stenoses of the spinal canal end/or other constrictions of the spinal canal comprising a microinvasive access tube having a distal end insertable into the body, an ablation device having an ablation head which can be accommodated in the access tube and can be directed out of the access tube at the distal end and brought into at least one working position, a screening element for screening the ablation head in fetetion to the dura which can be accommodated in the access tube and can be directed out of the access tube at the distal end and brought into at least one working position in which the screening element laterally protrudes above the access tube.

On the other hand, the object of the invention is, according to the invention, solved by an instrument set for the microinvasive treatment of stenoses of the spinal canal and/or other constrictions of the spinal canal comprising an ablation device having an ablation head which can be accommodated in a microinvasive access tube having a distal end insertable into the body and can be directed out of the access tube at the distal end and brought into at least one working position, a screening element for screening the ablation head in relation to the dura which can be accommodated in the microinvasive access tube and directed out of the access tube at the distal end and brought into at least one working position in which the screening element laterally protrudes above the access tube.

Other advantageous embodiments of the invention will be described with reference to embodiments which are predominantly described with reference to the drawing.

Figure 3A:
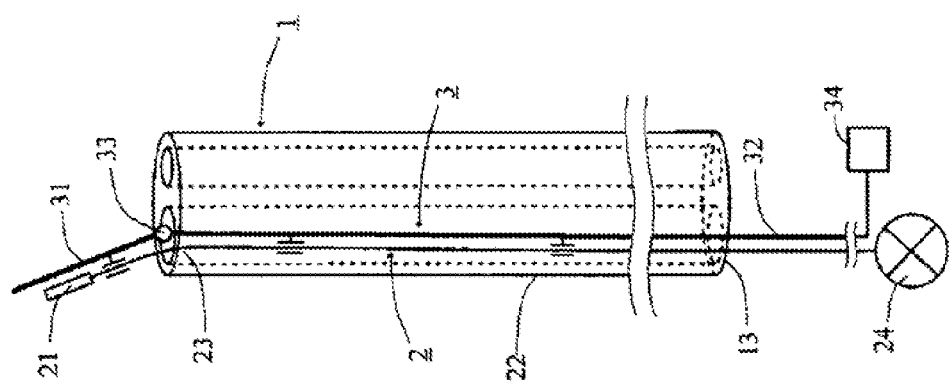
FIG. 3A shows an instrument set for the microinvasive ablation of stenoses of the spinal canal according to an embodiment of the invention in a first state.
Figure 5:
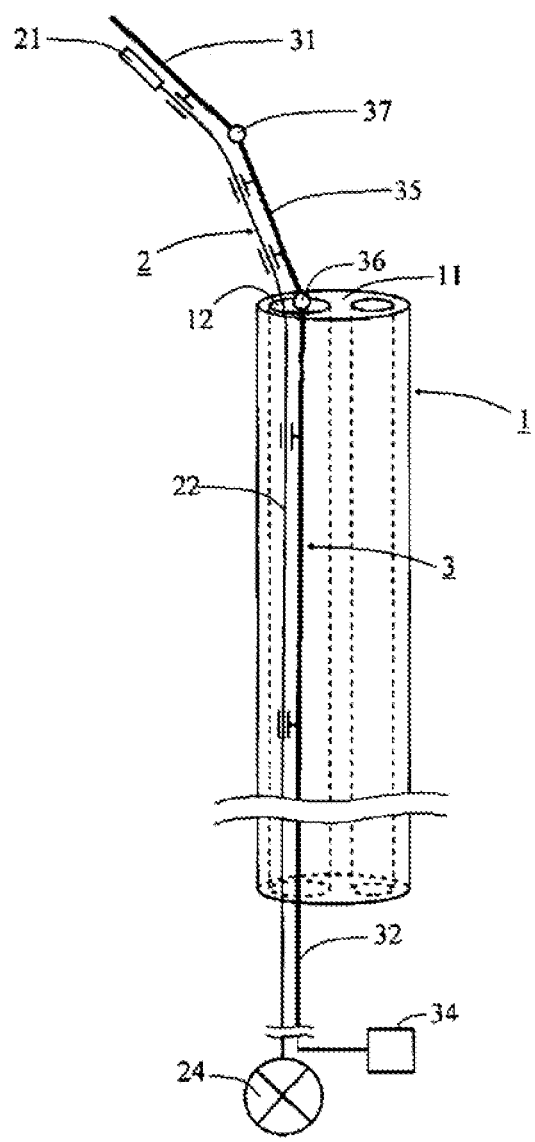
Figure 6:
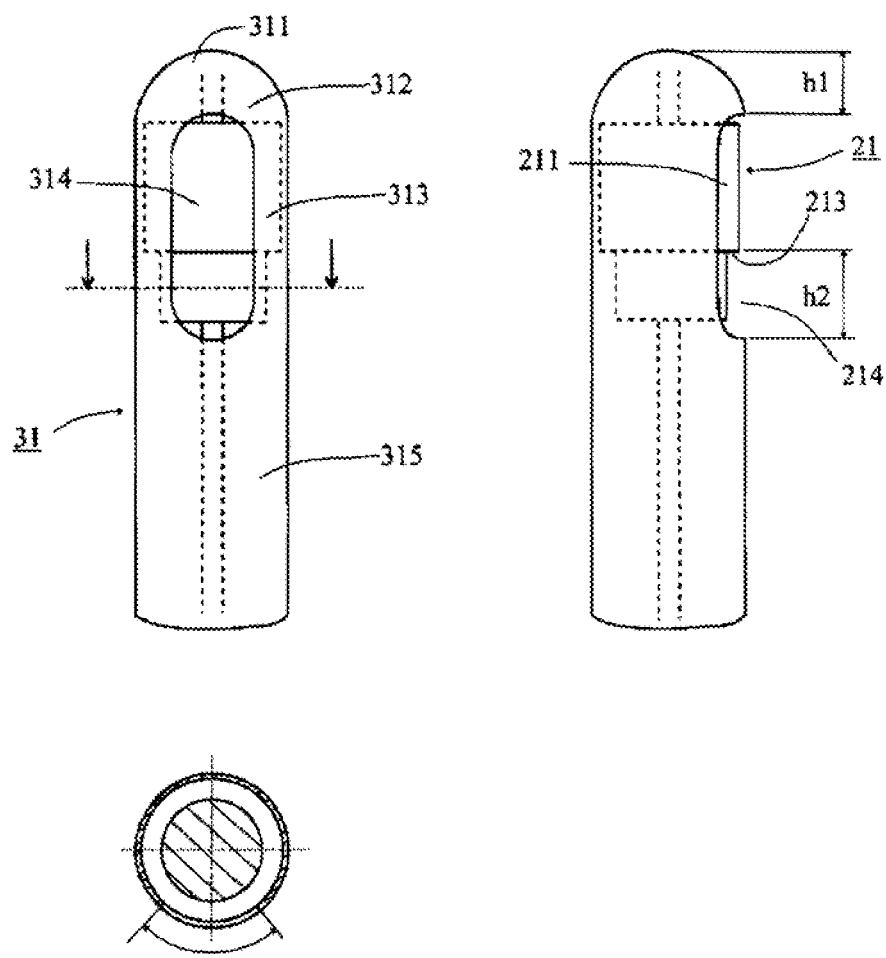
Figure 7:
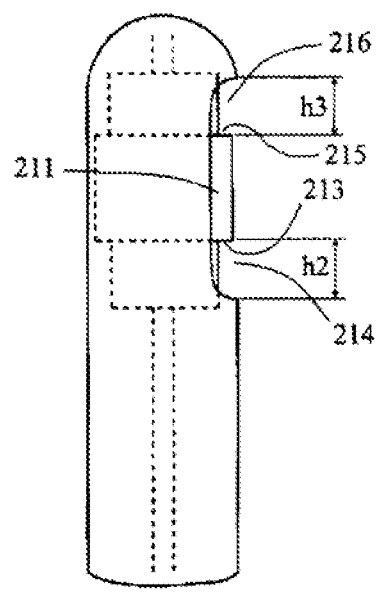
Figure 8:
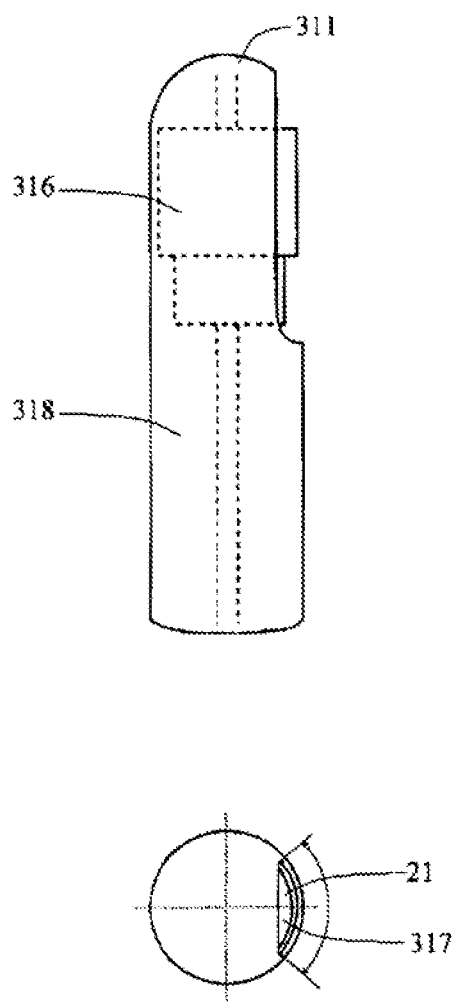

FIGS. 4A to D show steps of an application of the instrument set for the microinvasive ablation of stenoses of the spinal canal according to FIGS. 3A and B;

FIG. 5 shows an instrument set for the microinvasive ablation of stenoses of the spinal canal according to a further embodiment of the invention;

FIG. 6 shows an ablation head and a screening element of the instrument set for the microinvasive ablation of stenoses of the spinal canal and/or other constrictions of the spinal canal according to an embodiment of the invention;

FIG. 7 shows an ablation head and a screening element of the instrument set for the microinvasive ablation of stenoses of the spinal canal and/or other constrictions of the spinal canal according to another embodiment of the invention;

FIG. 8 shows an ablation head and a screening element of the instrument set for the microinvasive ablation of stenoses of the spinal canal and/or other constrictions of the spinal canal according to another embodiment of the invention;

FIG. 9 shows an embodiment of a control device of a screening element of the instrument set according to the invention for the microinvasive ablation of stenoses of the spinal canal according to an embodiment of the invention.

Figure 3B:
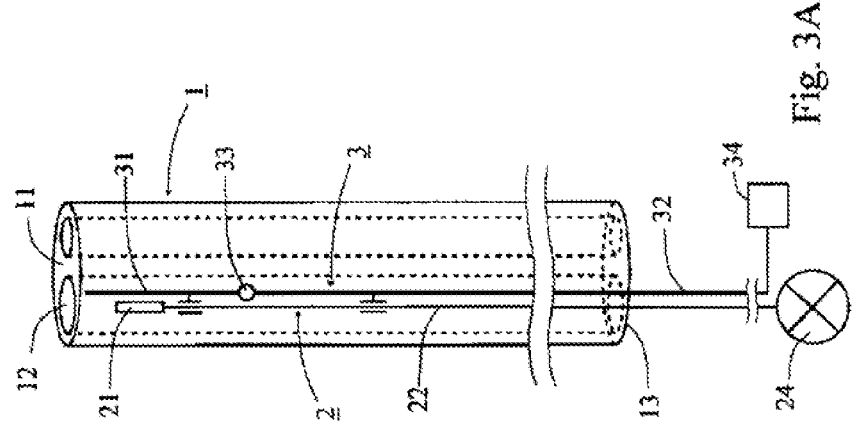
FIG. 3B shows the instrument set according to FIG. 3A in a second state.

FIGS. 3A and 3B show an instrument set for the microinvasive ablation of stenoses of the spinal canal and/or other constrictions of the spinal canal according to an embodiment of the invention. The instrument set comprises an ablation device 2 and a screening device 3. The instrument set is used in connection with a microinvasive access tube 1 having a distal end 11 insertable into the body and a cylindrical first working passage 12 capable of accommodating the ablation device 2 and the screening device 3. The access tube 1 may be specifically designed for the cooperation with the ablation device 2 and the screening device 3, or it may be a standard tubule. The access tube 1 may or may not be part of the instrument set for the microinvasive ablation of stenoses of the spinal canal.

The ablation device 2 comprises an ablation head 21 and a shaft 22. The screening device 3 comprises a screening element 31 and an elongated mount 32. The screening element 31 is supported on the elongated mount 32 via a joint 33. At its proximal end, i.e. at the end facing the surgeon, the screening device 3 comprises a control device 34 which can be used to cause the screening element 31 to be pivoted with respect to the elongated mount 32 at the joint 33. The shaft 22 extends along the elongated mount 32 and the screening element 31 and is supported on the former or the latter or both. At its proximal end, i.e. at the end facing the surgeon, the shaft 22 is connected to a drive 24. The ablation device 2 is mounted on the screening device 3 so that the ablation head 21 is positioned in the area of the screening element 31. Here, the ablation head 21 and the screening element 31 are designed and arranged with respect to each other so that the screening element 31 is capable of screening relevant sections of the ablation head 21 with regard to the surroundings.

As can be seen in FIG. 3A, the ablation device 2 may assume a posture in which the shaft 22 is straight and the shaft 22 and the ablation head 21 are aligned. The screening device 3 may assume a posture in which the elongated mount 32 and the screening element 31 substantially extend along a straight line and are aligned. If the ablation device 2 and the screening device 3 assume this positions they can be inserted into the first working passage 12 of the access tube 1 from the proximal end 13, i.e. from the end of the access tube 1 facing the surgeon. The ablation device 2 and the screening device 3 as well as the first working passage 12 are with regard to their dimensions, matched so that the ablation device 2 and the screening device 3 are substantially fully accommodated in the first working passage 12 as shown in FIG. 3A. In particular, the ablation head 21 and the screening element 31 are substantially fully accommodated in the first working passage 12.

The ablation device 2, the screening device 3, and the access tube 1 are designed so that the ablation head 21 or the screening element 31 can be directed outside at the distal end, i.e. at the end 11 of the access tube 1 facing the surgery location. In this way the ablation head 21 can be directed into different working positions. The screening element 31 can also be directed into different working positions in this way. A first working position of the ablation head 21 and a first working position of the screening element 31 are shown in FIG. 3B. The ablation head 21 and the screening element 31 are inclined with respect to the centre line of the access tube 1 in the first working position or in the first working posture and protrude sideways (laterally) with respect to the imagined extension of the access tube 1. The shaft 22 assumes a pivoted form in this situation. It may, e.g., be flexible and form a curve 23 in this situation. Alternatively, it may have a joint, e.g. a universal joint, and is pivoted in this situation. The screening element 31 is then pivoted with respect to the elongated mount 32 at the joint 33. The ablation head 21 and the screening element 31 may assume further working positions or working postures in which they are more or less pivoted.

The ablation device 2 may be a cutting device comprising a cutting head and a cutter shaft. Likewise, it may, for example, also be a planing, grinding, milling or other device suitable for ablating bone and/or tissue material.

The access tube 1 has a substantially cylindrical form. The working passage 12 extending in longitudinal direction has a substantially uniform cross section. The working passage 12 is dimensioned so that the ablation device 2 and the screening device 3, particularly the ablation head 21 and the screening element 31, can be inserted into the working passage 12 from the proximal end and directed out of it at the distal end.

Other embodiments of the instrument set according to the invention are formed by modifying, replacing by other elements and/or omitting individual or a plurality of elements of the instrument set described above.

FIGS. 4A to D show steps of an example of a surgical process rendered possible by the instrument set according to the embodiment described above and by other embodiments of the invention.

The patient is lying on the side. Starting from a lateral back area an access path to the foramen intervertebrale is established which is suitable for inserting the access tube 1.

Figure 4:
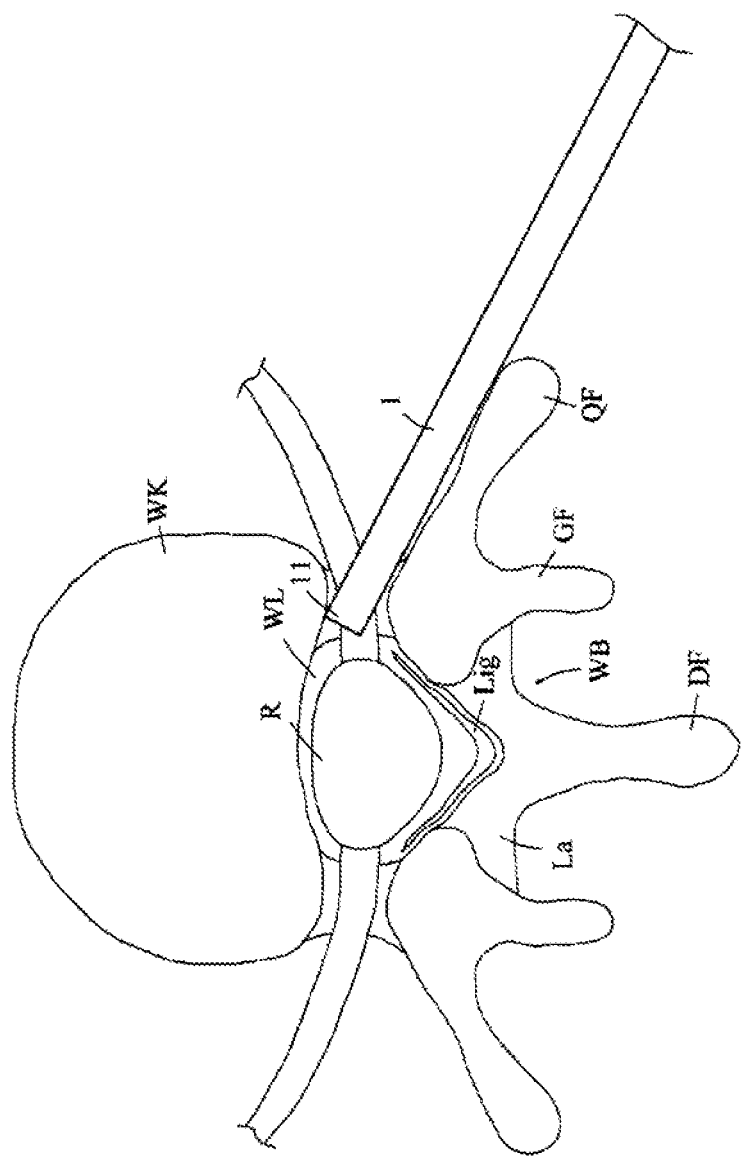
Figure 4B:
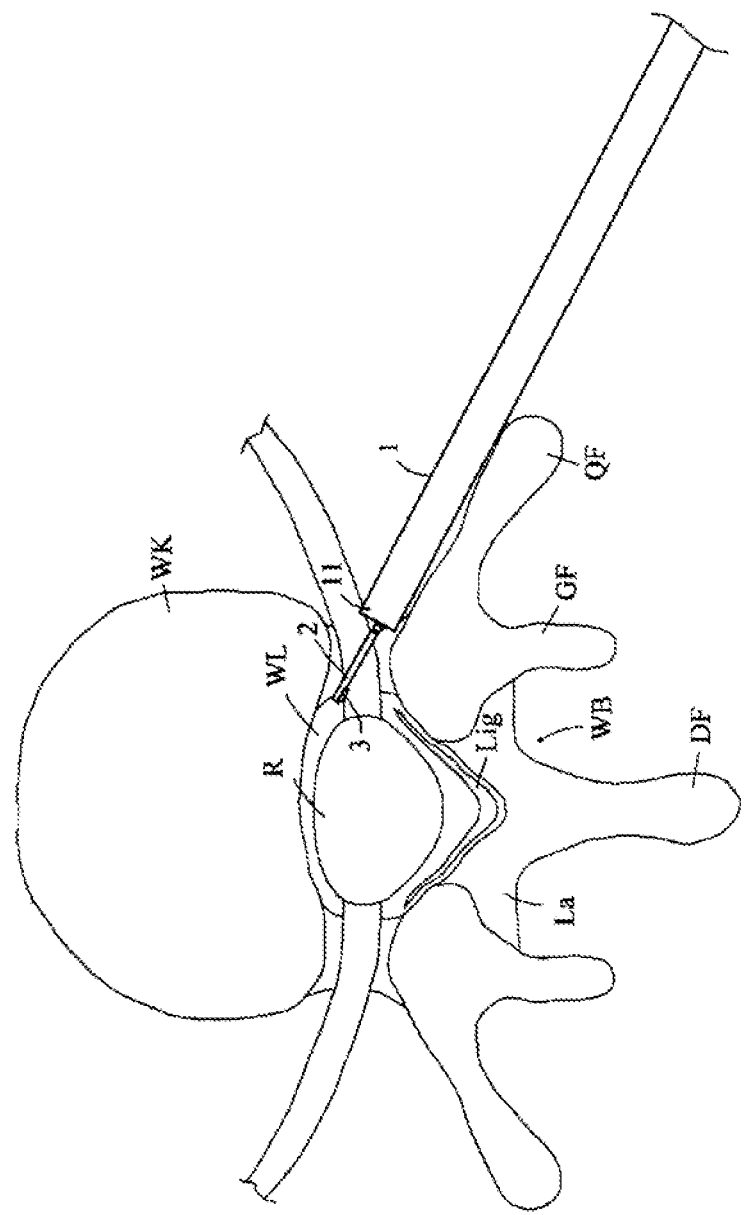

The access tube 1 is inserted into the foramen intervertebrale through this access path. Preferably, the access tube 1 is inserted thus far that it gets into the sector of the dura. It is particularly preferable that the access tube 1 is inserted until its distal end 11 abuts on the vertebral body as shown in FIG. 4A.

The access tube 1 will then be retracted by a defined distance. This distance may, for example, be defined so that the distal end 11 of the access tube 1 is positioned in a distance from the dura which is equal to the length of the screening element 31.

Thereafter, the screening element 31 is pushed forward by a distance in the direction of the dura from the distal end 11 of the access tube 1 so that the position shown in FIG. 48 is assumed.

Then the screening element 31 is pivoted by operating the control device 34 and in this way directed past the dura toward the dorsal side of the vertebra.

Figure 4C:
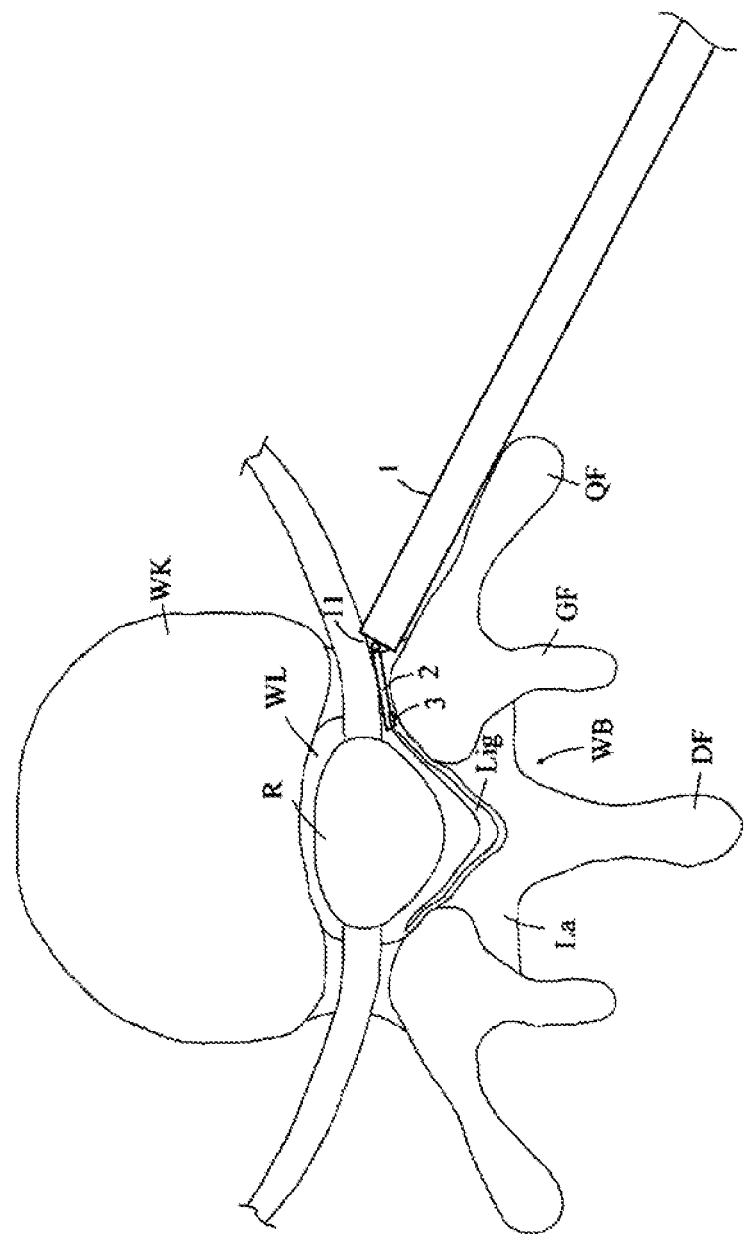
Figure 4D:
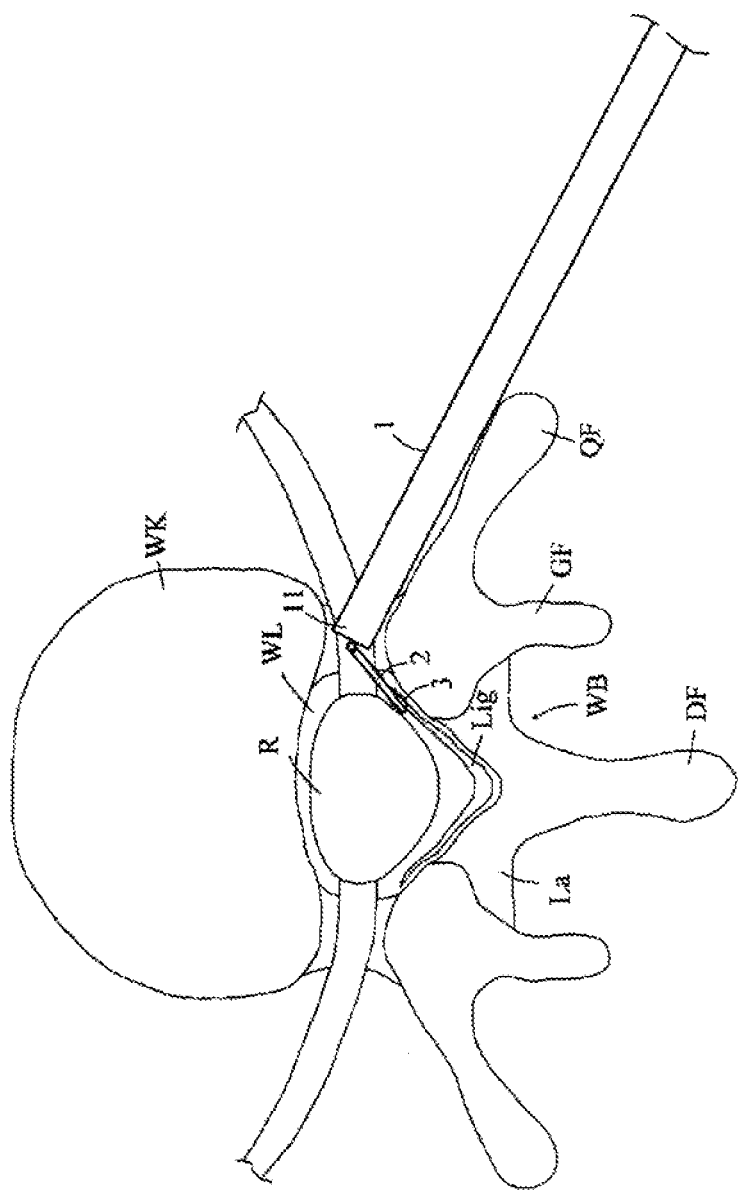

As shown in FIG. 4C, the screening element 31 is pivoted to the extent that the distal end of the screening element 31 comes to be positioned in the area between the dura and the vertebral arch.

As soon as the distal end of the screening element 31 in positioned in this area the screening element 31 can be further inserted into the clearance between of the dura and the vertebral arch as shown in FIG. 4D by again pushing the access tube 1 a little further into the foramen intervertebrale and, at the same time, further pivoting the screening element 31. The two movements can also be effected in turns. Preferably they are carried out alternatingly and repeatedly.

If the movement of the screening element 31 towards the clearance between the dura and the vertebral arch or into said clearance is blocked by ossifications or other callous structures these may be ablated by means of the ablation device 2.

FIG. 5 shows an instrument set for the microinvasive ablation of stenoses of the spinal canal and/or other constrictions of the spinal canal according to another embodiment of the invention. The instrument set according to this embodiment differs from the instrument set according to FIGS. 3A and 3B in that an intermediate element 35 is provided between the elongated mount 32 and the screening element 31. The intermediate element 35 is pivotable with respect to the elongated mount 32 via a joint 36. The screening element 31 is pivotably mounted on the intermediate element 35 via a joint 37. At its proximal end, i.e. at the end facing the surgeon, the screening element 3 is provided with a control device 34 which may be used to cause the screening element 31 to be pivoted with respect to the intermediate element 35 at the joint 37, and to cause the intermediate element 35 to be pivoted with regard to the elongated mount 32 at the joint 36. In FIG. 5, the instrument set according to this embodiment is shown in a state equivalent to the state of the embodiment described above which is shown in FIG. 3B. That means that the ablation head 21 is positioned in a first working position and that the screening element 31 is positioned in a first working position.

One example of a surgical process rendered possible by the instrument set according to this embodiment of the invention can be described as follows:

First, a process equivalent to the above description with reference to FIGS. 4A to 4D is carried out, however, under the provision that the screening element 31 is, on the one hand, pivoted with respect to the elongated mount 32 and, on the other hand, the intermediate element 35 and that the elongated mount 32 and the intermediate element 35 remain aligned with respect to each other.

When the screening element 31 has been inserted into the clearance between the dura and the vertebral arch in this way the access tube 1 is again retracted by a defined distance. This distance may, e.g., be defined so that it is equal to the length of the intermediate element 35 so that just the joint 36 protrudes beyond the access tube 1.

Then the intermediate element 35 is pivoted by operating the control device 34, and directed past the dura towards the dorsal side of the vertebra in this way. At the same time, the pivoted position of the screening element 31 with respect to the intermediate element 35 can be changed using the control device 34. Typically, the pivoting angle is reduced. By virtue of the interaction of the two pivoting movements the screening element 31 is further inserted into the gap between the dura and the vertebral arch. Here, the intermediate element 35 may be pivoted to the extent that also the distal end of the intermediate element 35 comes to be positioned in the area between of the dura and the vertebral arch.

As soon as the distal end of the intermediate element 35 is positioned in the area between the dura and the vertebral arch the screening element 31 and the intermediate element 35 can be further inserted into the clearance between the dura and the vertebral arch by again pushing the access tube 1 a little further forward into the foramen intervertebrale and, at the same time, further pivoting the intermediate element 35. In the meantime, the pivoting angle between the intermediate element 35 and the screening element 31 is further reduced, if required. The movements for inserting the access tube 1 and for pivoting the intermediate element 35 and for changing the pivoting angle between the intermediate element 35 and the screening element 31 may also be effected in turns. Preferably they are effected repeatedly and in turns.

To the extent the movement of the screening element 31 further towards or into the clearance between the dura and the vertebral arch is blocked by ossifications or other callous structures these are removed by means of the ablation device 2.

Further embodiments of the instrument set according to the invention (not shown in the Figures) are formed by providing an additional intermediate element or a plurality of additional intermediate elements which are respectively hinged via joints and further enhance the mobility between the screening element 31 and the elongated mount 32 in addition to the intermediate element 35. The insertion of the screening element 31 into the clearance between the dura and the ligamentum flavum is effected according to the same principle as in case of the embodiments described above.

Other embodiments of the instrument set according to the invention (not shown in the Figures) are formed by using a different design for the access tube 1 than in the embodiments described with reference to FIGS. 3 and 5. In a preferable embodiment the first working passage 12 provided in the access tube 1 comprises a distal section remote from surgeon in which the first working passage 12 is wider to accommodate the ablation head 21 and/or the screening element 31, and a proximal section in which the first working passage 12 is narrower. In another preferred embodiment the first working passage 12 comprises a distal orifice extending along a part of the face side of the access tube 1 as well as along a part of the lateral surface of the access tube 1. Preferably an axially extending slot is formed in the lateral surface on one side at the distal end of the access tube. This orifice also extending to the lateral surface serves to render it possible to already pivot the screening element 31 and the ablation head 21 before the screening device 3 is advanced so far that the joint 33, the joint 36 and/or the joint 37 protrude(s) from the access tube 1. Further, the designs are preferably combined with a further and a narrower section of the first working passage 12 and with an orifice also extending to the lateral surface.

The instrument set for a microinvasive ablation of stenoses of the spinal canal and/or other constrictions of the spinal canal may comprise endoscopic optics (not shown in the Figures). This optics enable the performance of the surgical process on sight. To move the optics into a position in which imaging of the work area of the ablation head 21 and of the area in which the pivoting movements of the screening element 31 take place are enabled the access tube 1 may have a second working passage through which the endoscopic optics are passed. In this way, particularly, sight on the dura and the nerve pathways passing through the foramen intervertebrale may be rendered possible. In this way it may be ensured that the movements of the ablation head 21 and of the screening element 31 are guided so that the dura and the nerve pathways are not injured.

The access tube 1 may then have a total of four or more passages, e.g. the first working passage 12, the second working passage and two rinsing passages and potentially one or more other passages for other functions.

Preferably, the access tube 1 is terminated by a cut face forming an angle of at least 20°, more preferably at least 40°, with a plane perpendicular to the longitudinal axis of the access tube 1 at its face side. Preferably, it is an elliptical cut face as formed by a diagonal cut of a cylinder tube. Preferably, the second working passage provided for passing through the optics ends in the area of the end of the elliptic cut face in the longitudinal direction which protrudes the furthest in the direction of the axis of the access tube 1, i.e. the protruding end of the ellipse. The first working passage 12 ends in the area of the opposite end of the elliptic cut face, i.e. the sloping end of the ellipse. Here, the first working passage 12 and the second working passage may be staggered in the transverse direction of the elliptic cut face, e.g. with the centre point of the first working passage 12 to the left of the longer axis of the elliptic cut face, and the centre point of the second working passage to the right of the longer axis. In this way it is ensured that, at the same time, a good sight on the work area of the ablation device 2, the dura and the nerve pathways is guaranteed and the optics are prevented from impeding the sequences of movements when positioning the ablation head 21 and the screening element 31.

In another embodiment (not shown in the Figures) the instrument set according to the invention for the microinvasive ablation of stenoses of the spinal canal comprises an access tube 1 in which the first working passage 12 is designed to accommodate the ablation device 2 and a third working passage (not shown in the Figures) different from the first one is provided which is designed for accommodating the screening device 3. The shaft 22 may be supported by bearing positions provided in the first working passage 12. The elongated mount 32 may be supported by bearing positions provided in the third working passage.

The access tube 1 may then have a total number of five or more passages, e.g. the first working passage 12, the second working passage for passing through optics, the third working passage, one or two rinsing passages and, if required, one or more further passages for other functions.

In the following, the ablation head 21 and the screening element 31 of the instrument set for the microinvasive ablation of stenoses of the spinal canal and/or other constrictions of the spinal canal according to an embodiment of the invention will be described with reference to FIG. 6. In the embodiment shown in FIG. 6 the ablation device 2 is a cutting device, and the ablation head 21 is a cutting head. The screening element 31 is formed so that it screens substantial parts of the ablation head 21. The screening element 31 includes a face portion 311 covering the entire radial/azimuthal cross section of the ablation head 21 at the distal end. The screening element 31 further preferably comprises an upper jacket part 312 covering the ablation head 21 and possibly its support over the entire circumference. Then, the screening element 31 comprises a central jacket part 313 covering the ablation head 21 over part of the circumference. In the central jacket part 313 a window 314 is provided which extends over part of the circumference and behind which the ablation head 21 is exposed. Finally, the screening element 31 preferably comprises a lower jacket part 315 in turn covering the ablation head 21 and possibly its support over the entire circumference. The geometry thus described has the advantage that the ablation head 21 is, in the sections located in the front during the advance, sufficiently screened by the face portion 311 and possibly the upper jacket part 312 to protect the dura during the advance of the ablation device 2 and the screening device 3 into the clearance between the dura and the ligamentum flavum illustrated in FIGS. 4C and 4D. On the other hand, the section in which the ablation head 21 becomes effective and can remove material follows in just a relatively short distance behind the tip of the screening element 31 provided with the window 314. Preferably, the distance h1 between the distal end of the screening device 3 and the upper end of the effective part of the ablation head 21 is at least 2 mm, preferably at least 4 mm, more preferably at least 6 mm. The screening element 31 may be integrally formed or be constituted by a plurality of parts. The same applies to each single one of the components of the ablation device 2 and of the screening device 3 described here.

In the embodiment according to FIG. 6 the ablation head 21 comprises a cutting section 211 having a cylindrical basic shape. The cutting section 211 is terminated by a proximal cutter ledge 213 towards the proximal end (the end located closer to the shaft 22). Preferably, the diameter of the ablation head 21 is reduced by at least 0.5 mm, preferably by at least 1 mm, more preferably by at least 2 mm at this proximal cutter ledge 213. The proximal cutter ledge 213 is followed by a proximal clearance section 214 in which the ablation device 2 retreats by at least the mentioned values with respect to the cutting section 211 and is at the same time exposed in the window 314. This clearance section 214 has a length h2 of at least 2 mm, preferably of at least 4 mm, more preferably of at least 6 mm.

The thus described geometry is advantageous in that the risk of injuring the dura is reduced while, at the same time a particularly effective ablation of stenoses as well as other bone and tissue material is rendered possible. The screening device 3 and the ablation device 2 are inserted into the clearance between the dura and the ligamentum flavum, e.g. by means of the technique described above with reference to FIGS. 4A to D. Here, the ablation head 21 is first directed past a zone to be ablated. The drive of the ablation device 2 may or may not be already turned on then. Then, the ablation head 21 in the clearance between of the dura and the ligamentum flavum is again retracted in the direction of the foramen intervertebrale with the drive turned on. At the same time, the ablation head 21 may be pressed against the ligamentum flavum or into stenoses or against other bone or tissue structures existing in its vicinity by operating the control device 34 of the screening element 31. This results in a particularly effective removal of material, particularly at the proximal cutter ledge 213, but also at the circumferential surface of the cutter section 211. With the proximal clearance section 214 it is promoted that the proximal cutter ledge 213 comes in a good contact with the structures to be removed since the above structures may protrude into the proximal clearance section 214. Owing to the fact that the ablation is performed by a rearward movement and at a side of the ablation head 21 which faces away from the dura, it is promoted that, in case of a correct handling, no injuries of the dura will occur.

In this embodiment the screening element 31 has a circular cross section. The opening angle of the window 314 ranges between 60° and 180°, preferably between 80° and 150°, more preferably between 100° and 120°. In this way it is promoted that, in case of a correct handling, no injuries of the dura can occur, and that at the same time an effective ablation is achieved.

FIG. 7 shows a further embodiment of the ablation device 2 and the screening element 31. In the embodiment shown in FIG. 7 as well the ablation device 2 is a cutting device and the ablation head 21 a cutting head. The screening element 31 is, to the largest extent, designed exactly as in the embodiment described with reference to FIG. 6. The ablation head 21 also has a similar design. It also comprises a cutting section 211 having a cylindrical basic shape. In contrast to the embodiment according to FIG. 6, the cutting section 211 is terminated by a distal cutter ledge 215 towards the distal end in the embodiment according to FIG. 7. This distal cutter ledge 215 may preferably be provided as an alternative to and particularly preferably in addition to the proximal cutter ledge 215. Preferably, the diameter of the ablation head 21 decreases by at least 0.5 mm, more preferably by at least 1 mm, even more preferably by at least 2 mm at the distal cutter ledge 215. Towards the distal end, the distal cutter ledge 215 is followed by a distal clearance section 216 in which the ablation head 21 is retracted by at least the mentioned values with regard to the cutting section 211, and is, at the same time, exposed in the window 314. This distal clearance section 216 has a length h3 of at least 2 mm, preferably of at least 4 mm, more preferably of at least 6 mm.

The ablation head 21 and the screening element 31 according to this embodiment enable a particularly effective ablation even during their advancement into the clearance between the dura and the ligamentum flavum. This is advantageous in that the risk that an obstacle, e.g. in the form of a stenosis, prevents a further advance of the screening element 31 and the ablation head 21 is kept low. If such an obstacle is in the way the screening element 31 and the ablation head 21 only have to be squeezed past the obstacle by a small distance until the obstacle can be worked on or removed by means of the ablation head 21. The screening device 3 and the ablation device 2 comprising the screening element 31 or the ablation head 21 are advanced into the clearance between the dura and the ligamentum flavum, e.g. by means of the technique described above with reference to FIGS. 4A to D. The drive of the ablation device 2 may or may not already be activated here. At the same time, the ablation head 21 may be pressed against the ligamentum flavum or stenoses existing in its vicinity or against other bone or tissue structures by operating the control device 34 of the screening element 31. This results in a particularly effective removal of material, particularly at the distal cutter ledge 215, but also at the circumferential surface of the cutter section 211. With the upper clearance section 216 it is promoted that the distal cutter ledge 215 gets into a good contact with the structures to be removed since protruding structures may protrude into the distal clearance section 216.

FIG. 8 shows yet another embodiment of the ablation head 21 and the screening element 31. In the embodiment shown in FIG. 8 the ablation device 2 is also a cutting device, and the ablation head 21 is a cutting head. Like in the embodiments according to FIGS. 6 and 7 the screening element 31 is formed so that it screens substantial portions of the ablation device 2. The screening element 31 further also comprises a face portion 311 at the distal end. In contrast to the embodiments according to FIGS. 6 and 7, however, the face portion 311 does not cover the entire radial/azimuthal cross section of the ablation head 21 in the embodiment according to FIG. 8. Rather, part of the ablation head 21 is exposed toward the face side. In the distal jacket part 316 following the face side a recess 317 is provided which extends across part of the circumference and is exposed behind the ablation head 21. Further, a proximal jacket part 318 may follow which covers the ablation head 21 and, potentially, its support over the entire circumference. The angle range across which the recess 317 extends is from 6° to 180°, preferably from 80° to 150°, more preferably from 100° to 120°.

The geometry thus described is advantageous in that the ablation head 21 is exposed practically directly at the tip of the screening element 31 and material can be effectively removed. This is advantageous in that the risk that an obstacle, e.g. in the form of a stenosis, prevents a further advancement of the screening element 31 and of the ablation head 21 is kept low if such an obstacle is in the way it will contact the ablation head 21 partly exposed at the face side of the screening device 3 and is therefore removed until it does no longer impede a further advance. At the same time the distal jacket part 316 covers the ablation head 21 along the larger part of the circumference and prevents the dura from being injured by the ablation head 21 in this area.

In other embodiments according to the invention the screening element 31 comprises at least one wall screening the ablation head 21 towards the side of the dura, and it preferably comprises a section which laterally screens the ablation head 21 at its lateral edges extending from the proximal end to the distal end. Incidentally or irrespective of this, the screening element 31 preferably has a curved progression from its proximal end to the distal end. Further, the screening element 31 preferably has an S-shaped, curved progression from its proximal end to the distal end so that the distal end is curved in the in pivoting direction and that a longer arc curved in the opposite direction follows towards the proximal end. Preferably, the screening element 31 surrounds the ablation head 21 to a large extent and is provided with a window-like recess in which the ablation head 21 is exposed at the side towards which the screening element 31 is moved when it is directed out or the access tube 1 and brought into the working position.

The position of ablation head 21 on the screening element 31 is preferably adjustable in the embodiments shown in FIGS. 6 to 8 but also in other embodiments. Particularly, adjustability in the longitudinal direction of the screening element 31 may be contemplated. What is meant by the longitudinal direction here is the dimensions from the proximal end of the screening element 31 to the distal end of the screening element 31. Likewise or in addition, adjustability in the transverse direction of the screening element 31 may be contemplated. Preferably, the ablation head 21 is adjustable beyond the distal edge of the screening element 31 and/or beyond a lateral edge or the lateral edges of the screening element 31. It is particularly preferable that the ablation head 21 is adjustable over the entire length of the screening element 31. Further, preferably, the orientation of the ablation head 21 is adjustable.

Preferably, the instrument set according to the invention comprises a plurality of different ablation devices 2 which are, depending on the requirements, used for specific ablation tasks.

FIGS. 9A and B show an embodiment of a control device 34 of a screening element 31 of an instrument set for the microinvasive ablation of stenoses of the spinal canal according to the invention. As can be seen in FIG. 9A, the elongated mount 32 is designed so that it is hollow in this embodiment. The proximal end of the screening element 31 is accommodated in the distal end section of the elongated mount 32. The joint 33 is formed by a bolt and a plain bearing. The bolt is fixedly and rotatably accommodated in bearing bores in the elongated mount 32 on the screening element 31 or fixedly and rotatably accommodated in bearing bores in the screening element 31 on the elongated mount 32. The joint 33 is provided on the one side of the hollow elongated mount 32. On the opposite side of the elongated mount 32 a hinging device in the form of another bolt 348 is provided on which an actuating wire 346 of the control device 34 engages. The actuating wire 346 is deflected by a deflector device 349 and, apart from that, extends in the hollow space of the hollow elongated mount 32 in its longitudinal direction. By pulling the actuating wire 346 the screening element 31 is pivoted about the joint 33 with respect to the elongated mount 32. The actuating wire 346 may be a rigid wire which can also transfer pressure forces to pivot the screening element 31 backwards. Alternatively a spring (not shown in the Figures) may be provided which pivots the screening element 31 back when no pulling force is exerted on the actuating wire 346.

At the proximal end of the elongated mount 32 a handle device is provided which is similar to a scissors handle as can be seen in FIG. 9B. A first handle element 341 having a first handle ring 344 for inserting the thumb of the surgeon is provided. A second handle element 342 comprising a second handle rind 345 for inserting the forefinger of the surgeon is provided. Like in scissors, the first handle element 341 for the thumb and the second handle element 342 for the forefinger are pivotable with respect to each other. To this end, another bolt 343 is fixedly mounted on the first handle element 341. This bolt 343 is accommodated by the second handle element 342 with the aid of a plain bearing. On the second handle element 342, further, in a distance to the bolt 343, another bolt 347 is provided to which the actuating wire 346 is attached. By moving the scissors-like handle elements 341 and 342 apart a pulling movement is exerted on the actuating wire 346. This pulling movement is then translated into a pivoting movement of the screening element 31 at the proximal end. On the first handle element 341 two stoppers 340 are provided which limit the mutual pivoting movement of the handle elements 341 and 342. The stoppers 340 are formed so that the pivoting movement of the screening element 31 between a position in which the screening element 31 and the elongated mount 32 are aligned and a maximally pivoted position is limited.

Now, a further embodiment of a control device 34 of a screening element 31 (not shown in the Figures) will be described. The control device 34 according to this embodiment may, e.g., be used for operating the embodiment of the instrument set for the microinvasive ablation of stenoses of the spinal canal described above with reference to FIG. 5. The control device 34 according to this embodiment is principally designed like in the embodiment described above with reference to FIG. 9, does, however, exhibit some differences and comprises additional components. Other than in the embodiment according to FIG. 9 the screening element 31 is pivoted with respect to the intermediate element 35 instead of with respect to the elongated mount 32 using the actuating wire 346, namely about the joint 37. For deflecting the actuating wire 346 another deflector device on the intermediate element 35 is provided instead of the deflector device 349 on the elongated mount 32 in this embodiment. Furthermore, other redirecting devices for the actuating wire 346 may exist, e.g. on the intermediate element 35 or on the elongated mount 32. Further, a second actuating wire engaging on another bolt provided on the intermediate element 35 near the joint 36 is provided. This second actuating wire may, e.g., be operated via a third handle element comprising a third handle ring for the middle finger.

Further embodiments of a control device 34 of a screening element 31 of an instrument set for the microinvasive ablation of stenoses of the spinal canal according to the invention are formed by providing an operation with the aid of actuators instead of a manual operation. Preferably, these actuators electronically controlled.

Further embodiments of the instrument set for the microinvasive ablation of stenoses of the spinal canal according to the invention comprise devices ensuring that the ablation head 21 and the screening element 31 are dorsally guided past the nerve cord (NS) on their way to the stenoses of the spinal canal.

Figure 1:
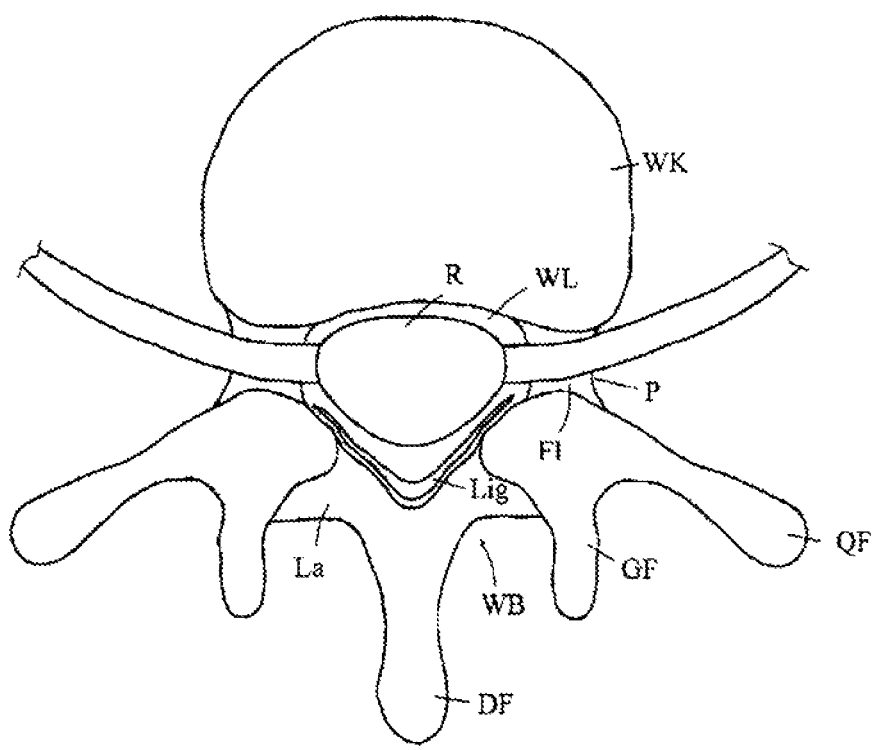
FIG. 1 shows the structure of a human vertebral body including an example for a stenosis of the spinal canal to be treated.
Figure 2:
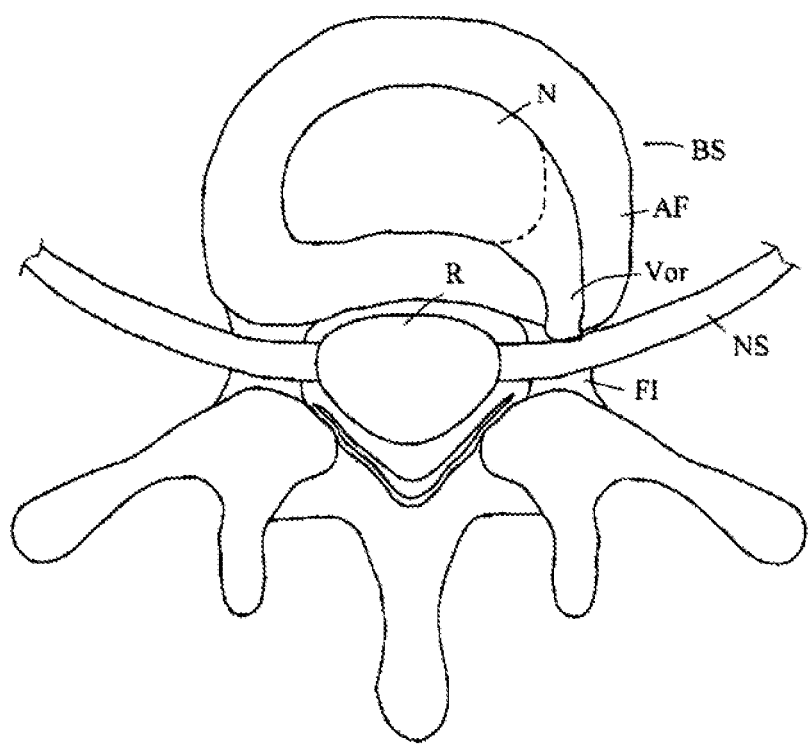
FIG. 2 shows the problem of a herniated disc.

It is advantageous that the ablation device 2 and the screening device 3 are dorsally directed past the nerve cord (NS) on the way to the stenoses of the spinal canal. In FIGS. 1 and 2 the ventrally positioned vertebral body (WK) and the dorsally positioned vertebral arch including the articular processes (GF) and the transverse processes (QF) can be discerned. In between, laterally, the orifice of the foramen intervertebrale (FI) is to be found. A nerve cord (NS) laterally branching away from spinal cord extends through the foramen intervertebrale (FI) When the instrument set according to the invention is applied, preferably, an access path for the instrument set for the microinvasive ablation of stenoses of the spinal canal is established which leads dorsally past the nerve cord (NS). When an access path leading dorsally past the nerve cord (NS) is established the screening element 31 will not only screen the ablation head 21 mainly exposed on the dorsal side during the application with respect to the spinal cord (dura) but also with respect to the nerve cord (NS). In this way the risk of injuring the nerve cord (NS) is reduced.

To accomplish that the ablation device 2 and the screening element 31 are directed dorsally past the nerve cord (NS) the instrument set according to one embodiment comprises a device for pushing away nerves (not shown in the Figures). Preferably, the device for pushing away nerves is formed as an elongated instrument designed to be directed through a working passage of the access tube 1. Preferably, the device for pushing away nerves has a slant (not shown) or a movable element capable of pushing a nerve card to the side in the area facing away from surgeon. The movable element may, for example, be a pivotable arm. A fourth working passage distinct from the first working passage 12 and potentially the second working passage for the optics and potentially the third working passage for a screening element 31 passed through separate from the ablation device 2 is provided in the access tube 1 for passing through the device for pushing away nerves. The access tube 1 may then comprise five or more passages, e.g. the first working passage 12, the second working passage for passing through optics, the fourth working passage and two rinsing passages, or even six or mare passages, e.g. the first working passage 12, the second working passage for passing through optics, the third working passage for passing through of the screening element 31, the fourth working passage and two rinsing passages.

Other embodiments of the instrument set according to the invention may further comprise am access path instrument set (not shown in the Figures) to accomplish that an access path directed dorsally past the nerve cord (NS) is established. The access path instrument set may, preferably, comprise a needle-shaped access path instrument formed as a surgical needle, preferably as a spinal needle. The needle-shaped access path instrument is inserted into the body in the direction towards the foramen intervertebrale starting from the side of the back. The needle-shaped access path instrument is inserted until the tip has reached the area of the foramen intervertebrale. Then other access path instruments belonging to the access path instrument set are used to widen the established access path. These other access path instruments are formed as dilatation tubes which are slid onto the needle-shaped access path instrument and potentially onto dilatation tubes previously slid on. Each dilatation tube has a larger outer diameter than the needle-shaped access path instrument and all dilatation tubes slid on before, and an inner diameter suitable for ac commodating the elements slid on before. The dilatation tubes may have a cutter-like profile on the face side to support the dissecting of the pierced tissue in case of a rotating operation.

The access path for the instrument set according to the invention is preferably selected so that it extends in a plane perpendicular to the longitudinal direction of the body angled at an angle of more than 70°, more preferably more than 80° with respect to the dorsal direction. The needle-shaped access path instrument, the device for pushing away nerves, the ablation device 2 and/or the screening device 3 are therefore inserted at a position located particularly far towards the outer side of the back. For this purpose, the needle-shaped access path instrument has a length of more than 15 cm, preferably more than 20 cm, more preferably more than 25 cm. For this purpose, the ablation device 2 has a length of more than 20 cm, preferably more than 25 cm, more preferably more than 30 cm. For this purpose, the screening device 3 has a length of more than 20 cm, preferably more than 25 cm, more preferably more than 30 cm.

Preferably, the needle-shaped access path instrument comprises a sensor array recording a physical variable or a plurality of physical variables suitable for determining the proximity and/or the relative position of nerve pathways in the area of its tip. The signals recorded by the sensor array are analysed by means of an evaluation unit, and the relative location of the access path instrument with respect to the nerve pathways is determined. This relative location may be shown on a monitor. Based on this display the surgeon can determine whether the needle-shaped access path instrument defining the access path is positioned at the dorsal or at the ventral side of the nerve cord (NS). If the access path instrument assumes a position at the undesired side of the nerve cord (NS) the surgeon can withdraw the needle-shaped access path instrument and reinsert it to reach the desired position. Based on the display the surgeon can further ensure that the access path instrument does not injure the nerve cord (NS).

Further the instrument set for the microinvasive ablation of stenoses of the spinal canal according to the invention may comprise an imaging device by which the location of the access path instrument, the device for pushing away nerves, the ablation device 2 and/or the screening device 3 is recorded. The imaging device may, for example, use the method of computed tomography (CT), magnetic resonance tomography (MRT), scintigraphy or native radiography. If a method unsuitable for tracing the location of the nerve cord (NS) like, e.g., computed tomography, is used an analysis device is used to determine the relative location of the access path instrument, the device for pushing away nerves, the ablation device and/or the screening device with regard to the nerve cord (NB). The analysis device has a memory in which data on the individual anatomic or geometric conditions at the operating position of the patient to be treated are stored. The data may have been previously gathered, for example by magnetic resonance tomography (MRT). From these data the analysis device prepares a representation of the nerve cord (NS) which corresponds to the image of the current position and location of the access path instrument, the device for pushing away nerves, the ablation device 2 and/or the screening device 3 furnished by the imaging device with regard to viewing angle, scale and other rendering parameters. The image of the respective instrument and the depiction of the nerve cord (NS) are then superimposed and displayed on a screen so that the surgeon can view the relative location of the access path instrument, the device for pushing away nerves, the ablation device 2 and/or the screening device on the one hand and the nerve cord (NS) on the other hand, assuming that the nerve cord (NS) has not shifted. The analysis device can be realised by an appropriate combination of computer hardware and software.

In other embodiments the instrument set for the microinvasive ablation of stenoses of the spinal canal according to the invention is provided with a control device (not shown in the Figures). If the instrument set comprises operating devices including actuating drives the control device can control the actuating drives by transmitting control instructions to it. This may be effected by means of cable-dependent or wireless transmission technology. If the instrument set comprises manual operating devices the control instructions prepared by the control device are output to the surgeon via an acoustic or visual output device like, e.g., an announcing device or a monitor. A control device for the instrument set described above with reference to FIG. 5 comprising the elongated mount 32, the screening element 31 and the intermediate element 35 may, e.g., output control instructions for:

advancing the access tube 1 into the foramen intervertebrale or for withdrawing it from the foramen intervertebrale;

advancing the screening element 31 out of the distal end 11 of the access tube 1 or withdrawing the screening element 31 into the access tube 1;

pivoting or returning the screening element 31 with respect to the intermediate element 35;

pivoting or returning the intermediate element 35 with respect to the elongated mount 32.

The control instructions output by the control device can be based on a pre-programmed moving program. Preferably data on the individual conditions pertaining to the patient such as, for example, the exact position and shape of the stenosis of the spinal canal, but also the exact dimensions of the vertebral body are taken into consideration in determining the control instructions. These data relating to the patient may be gathered by means of a common imaging method, e.g. computed tomography. Further, preferably also the exact size and shape of the instrument set are taken into consideration. Furthermore, preferably the current position of the instrument set and the current location and form of the vertebral body and of the stenosis of the spinal canal are recorded during the course of the surgery, and the program flow is adjusted correspondingly.

Now, an operating and control device of the instrument set for the microinvasive ablation of stenoses of the spinal canal according to the invention according to an embodiment of the invention will be described. This operating and control device completely or partly assumes the drive of the various movements of the instrument set and/or their control. The operating and control device comprises a processor, a data storage, a monitor as well as a first, a second, a third, a fourth and a fifth actuator. The first actuator drives a forward and withdrawal movement of the access tube 1. The second actuator drives a forward and withdrawal movement of the elongated mount 32. The third actuator drives a pivoting movement of the joint 36 between the elongated mount 32 and the intermediate element 35. The fourth actuator drives a pivoting movement of the joint 37 between the intermediate element 35 and the screening element 31. The fifth actuator drives a rotational movement of the ablation head 21 designed as a cutting head in this embodiment.

The data storage comprises a physiologic data storage in which the geometries and dimensions of the relevant parts of the body of the patient in the operation zone are stored, preferably in the form of high-definition 3D data as in a CAD-System. These data may have been gathered by conventional imaging methods such as, e.g., computed tomography (CT) or magnetic resonance tomography (MRT), scintigraphy, native radiography or the like, etc. Further, other physiologic data such as, e.g., data on the degree of hardening of an ossification, the density of specific zones etc. may be stored in the physiologic data storage. Further, the data storage includes an instrument data storage in which the geometries and dimensions of the used surgical instrument set are stored. These data as well are preferably available in the form of high-definition 3D data as in a CAD-System. The data storage further comprises an instrument position storage in which the current positions and locations of the used surgical instrument set are stored, organised according to the individual components of the instrument set. The data storage further comprises an actuator data storage in which the performance data of the actuators of the used surgical instrument set are stored. In addition, the data storage comprises an operation program storage in which control programs for specific sequences of movements performed by the components of the instrument set in the course of the operation are stored. These are preferably programs which take data from the physiologic data storage, the instrument data storage, the instrument position storage and/or the actuator data storage into consideration in the organisation of the sequence of movements.

The operating and control device further preferably comprises one or more programs for the operation control by the surgeon. Thus, preferably, an input screen is output on the monitor via which the operator, e.g. the surgeon, can select operation programs and/or determine individual operation steps which will then be executed by means of the instrument set including the operation and control device. The current position and location of the instrument set may also be displayed on the monitor by means of an imaging method.

According to the invention it is possible that the operating and control device controls and drives individual or a plurality of the abovementioned movements and processes, and that other processes and procedural steps are performed manually. Here it is, e.g., possible that the control program runs the automatically controlled and driven process and that the surgeon then indicates in the proper place that now specific manual work is required.

Other than for the microinvasive ablation of stenoses of the spinal canal the instrument set designed according to the invention may also be used for other microinvasive surgery on the spinal column or on other parts of the body. Preferably it is used for the microinvasive ablation of stenoses of the spinal canal, particularly at the ligamentum flavum.

The invention claimed is:

1. An instrument set for the microinvasive treatment of stenoses of a spinal canal and/or other constrictions of the spinal canal, comprising:
    an ablation device having an ablation head which can be accommodated in a microinvasive access tube having a distal end insertable into a body and which can be directed out of the access tube at the distal end and brought into at least one working position;
    a screening element for screening the ablation head in relation to a dura, which can be accommodated in the microinvasive access tube and which can be directed out of the access tube at the distal end and brought into at least one working position in which the screening element laterally protrudes above the access tube; wherein the screening element has a proximal end and a distal end and is part of a screening device which further comprises an elongated mount on which the screening element is directly or indirectly supported, wherein the elongated mount and the screening element are arranged so as to be substantially aligned with respect to each other in a first position of the screening element and the screening element is arranged so that it is pivoted with resect to the elongated mount in the working position; and
    at least one intermediate element between the elongated mount and the screening element, which intermediate element can be pivoted with respect to the elongated mount and on which intermediate element the screening element is pivotably disposed, wherein pivoting the intermediate element with respect to the elongated mount and pivoting the screening element with respect to the intermediate element can be done independent of each other.

2. The instrument set according to claim 1, wherein the screening element has a curved progression from its proximal end to its distal end.

3. The instrument set according to claim 1, wherein the screening element has an S-shaped, curved progression from its proximal end to its distal end so that the distal end is curved in the pivoting direction and that a longer arc curved in the opposite direction follows towards the proximal end.

4. The instrument set according to claim 1, wherein the screening element surrounds the ablation head to a large extent and is provided with a window-like recess in which the ablation head is exposed at a side towards which the screening element is directed when it is brought into the working position.

5. The instrument set according to claim 1, wherein the ablation head is formed as a cutting head and comprises a cutting section which is confined by a proximal cutter ledge at which a diameter of the ablation head decreases by at least 0.5 mm, towards the proximal end, and which is followed by a proximal clearance section of the ablation head which is exposed in a window-like recess, wherein the proximal clearance section has a length of at least 2 mm.

6. The instrument set according to claim 3 wherein the ablation device comprises a shaft that is supported on the screening element by means of a plurality of plain bearings or ball bearings.

7. The instrument set according to claim 1, wherein the ablation device comprises a shaft that is supported on a microinvasive access tube by means of at least one plain or ball bearing.

8. The instrument set according to claim 1, wherein the instrument set comprises endoscopic optics.

9. The instrument set according to claim 1, further comprising a microinvasive access tube having a distal end insertable into a body, which access tube has a distal end and such exterior dimensions at its distal end that it is insertable into a clearance between vertebral bodies through a foramen intervertebrale.

10. The instrument set according to claim 9, wherein the access tube has a circular exterior cross section of less than 12 mm.

11. The instrument set according to claim 9, wherein the access tube comprises at least five passages, including two working passages, a passage for passing through endoscopic optics, and two rinsing passages.

12. An instrument set for the microinvasive treatment of stenoses of a spinal canal and/or other constrictions of the spinal canal, comprising:
    an ablation device having an ablation head which can be accommodated in a microinvasive access tube having a distal end insertable into a body and which can be directed out of the access tube at the distal end and brought into at least one working position, and
    a screening element, with a distal edge and a lateral edge and a proximal end and a distal end for screening the ablation head in relation to a dura, which can be accommodated in the microinvasive access tube and which can be directed out of the access tube at the distal end of the access tube and brought into at least one working position in which the screening element laterally protrudes above the access tube,
wherein the screening element is part of a screening device which further comprises
    an elongated mount on which the screening element is directly or indirectly supported, wherein the elongated mount and the screening element are arranged so as to be substantially aligned with respect to each other in a first position of the screening element and the screening element is arranged so that it is pivoted with respect to the elongated mount in the working position, and
wherein the ablation device is supported on the screening element and a position of the ablation head relative to the screening element is adjustable, particularly in a longitudinal direction and/or in a transverse direction of the screening element.

13. The instrument set according to claim 12, wherein the ablation head is adjustable beyond the distal edge and/or the lateral edge of the screening element.

14. The instrument set, according to claim 12, wherein the screening element has a curved progression from its proximal end to its distal end.

15. The instrument set according to claim 12, wherein the screening element has an S-shaped, curved progression from its proximal end to its distal end so that the distal end is curved in the pivoting direction and that a longer arc curved in the opposite direction follows towards the proximal end.

16. An instrument set for the microinvasive treatment of stenoses of a spinal canal and/or other constrictions of the spinal canal, comprising:
    a microinvasive access tube having a distal end insertable into a body;
    an ablation device having an ablation head which can be accommodated in the access tube and which can be directed out of the access tube at the distal end and brought into at least one working position;
    a screening element for screening the ablation head in relation to a dura which can be accommodated in the access tube and which can be directed out of the access tube at the distal end and brought into at least one working position in which the screening element laterally protrudes above the access tube; and
    endoscopic optics;
wherein the ablation device comprises a shaft that is supported on the screening element and wherein the screening element is part of a screening device which further comprises
    an elongated mount on which the screening element is directly or indirectly supported, wherein the elongated mount and the screening element are arranged so as to be substantially aligned with respect to each other in a first position of the screening element, and the screening element is arranged so that it is pivoted with respect to the elongated mount in the working position, and
    at least one intermediate element between the elongated mount and the screening element which intermediate element can be pivoted with respect to the elongated mount and on which intermediate element the screening element is pivotably disposed, wherein pivoting the intermediate element with respect to the elongated mount and pivoting the screening element with respect to the intermediate element can be done independent of each other,
wherein the intermediate element can be pivoted with respect to the elongated mount away from an aligned configuration, while at the same time the screening element can be pivoted with respect to the intermediate element towards an aligned configuration, and the intermediate element is pivoted with respect to the elongated mount by means of a first manual operation element and the screening element is pivoted with respect to the intermediate element by means of a second manual operation element.

17. The instrument set according to claim 1, wherein the intermediate element can be pivoted with respect to the elongated mount away from an aligned configuration, while at the same time the screening element can be pivoted with respect to the intermediate element towards an aligned configuration.

18. The instrument set according to claim 1, wherein the intermediate element is pivoted with respect to the elongated mount by means of a first driving element and the screening element is pivoted with respect to the intermediate element by means of a second driving element.

19. The instrument set according to claim 1, wherein the intermediate element is pivoted with respect to the elongated mount by means of a first manual operation element and the screening element is pivoted with respect to the intermediate element by means of a second manual operation element.

20. The instrument set according to claim 1, wherein the ablation device is supported on the screening element and the position of the ablation head relative to the screening element is adjustable, particularly in a longitudinal direction and/or in a transverse direction of the screening element.

* * * * *